United States Patent [19]

Molt

[11] Patent Number: 4,574,647
[45] Date of Patent: Mar. 11, 1986

[54] AIR CONVEYING MEANS FOR GAS ANALYSIS TEST TUBES

[75] Inventor: Werner Molt, Berlin, Fed. Rep. of Germany

[73] Assignee: Auergesellschaft GmbH, Berlin, Fed. Rep. of Germany

[21] Appl. No.: 642,234

[22] Filed: Aug. 20, 1984

[30] Foreign Application Priority Data

Aug. 22, 1983 [DE] Fed. Rep. of Germany ....... 3330578

[51] Int. Cl.$^4$ ............................................. G01N 1/14
[52] U.S. Cl. .................................. 73/864.34; 417/63; 417/472
[58] Field of Search ........... 73/863.21, 863.23, 864.34; 235/91 R; 417/63, 472, 478; 422/83, 86, 99

[56] References Cited

U.S. PATENT DOCUMENTS 3,223,487  12/1965  Grosskopf ............................ 422/86
3,861,217   1/1975  Rabenecker ...................... 73/864.34

FOREIGN PATENT DOCUMENTS 1302037  7/1962  France ................................ 417/472
 597364  8/1959  Italy .................................... 417/472

Primary Examiner—S. Clement Swisher
Attorney, Agent, or Firm—Reed Smith Shaw & McClay

[57] ABSTRACT

An air conveyor for gas test tubes used in the detection of foreign gases or suspended matter in air having an instrument body in the form of a handle and including a channel therethrough. The body has at one end a sealing element for connecting the gas test tube to the channel and at its other end a suction element in the form of a bellows. A base plate is included to which the suction element is mounted and has an air outlet valve therethrough and in communication with the bellows. A counter ring means is mounted to and rotatable about said body and including a spring biased locking element. A control rod is connected to the base plate and positioned for guided movement in the channel, said control rod being arrestable when said suction element is empty and releasable to initiate a suction stroke of said suction element by rotation of such counter ring.

10 Claims, 4 Drawing Figures

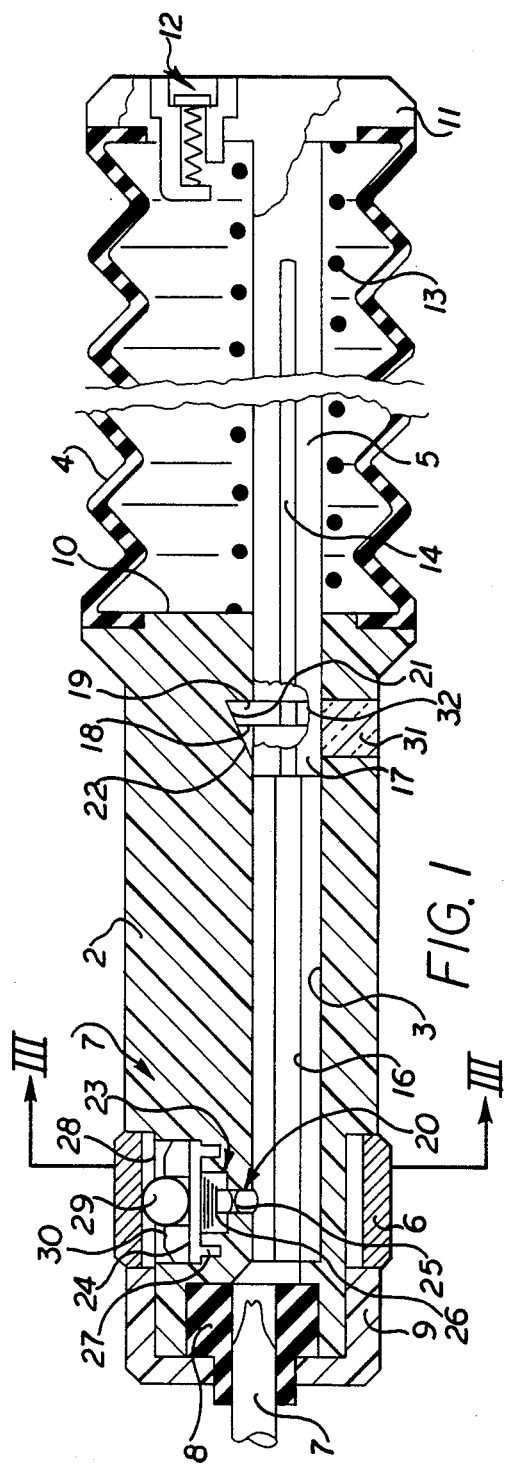
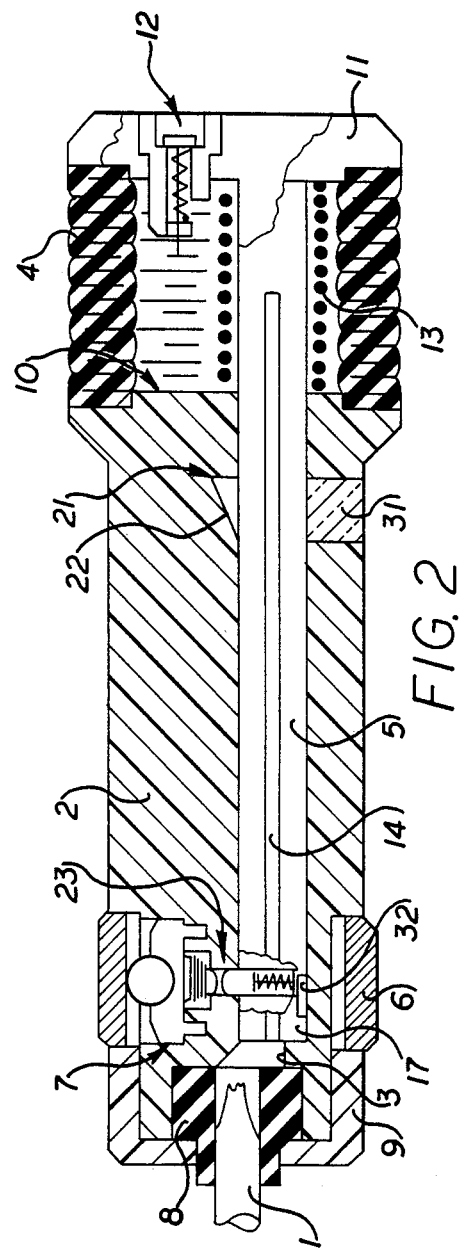

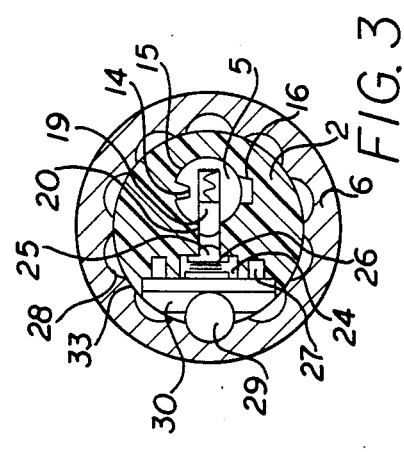
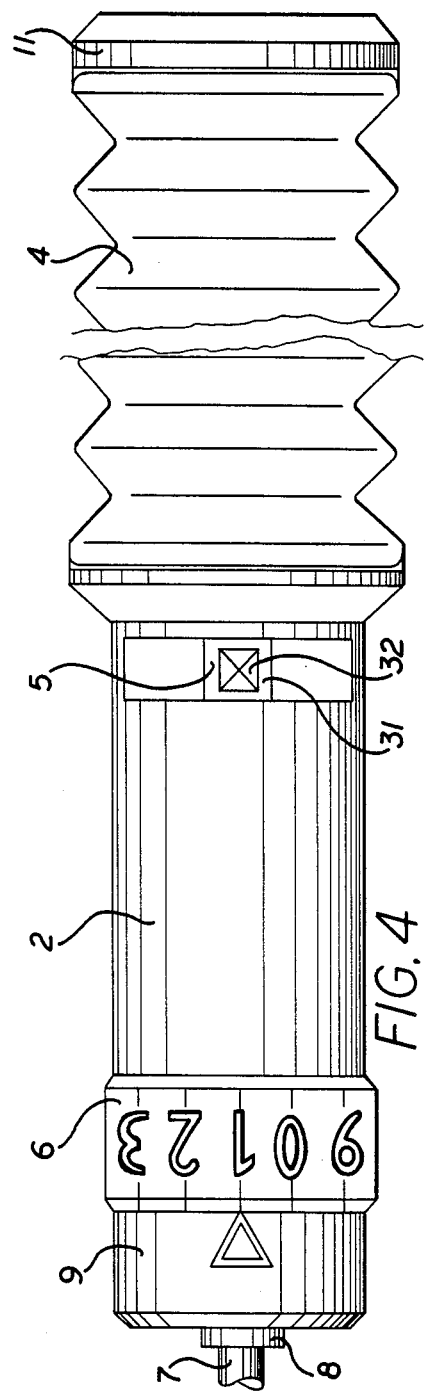

AIR CONVEYING MEANS FOR GAS ANALYSIS TEST TUBES

FIELD OF THE INVENTION

The present invention relates to a means for conveying to a test tube a gas for analysis, and, in particular, to a hand held suction conveyor for delivering to a test tube a reproducible amount and velocity of gas.

BACKGROUND OF THE INVENTION

In known air conveyors for use in delivering a gas through a test tube, the gas to be analyzed is drawn through the gas test tube by means of a suction element in the form of a rubber ball pump. The air escapes to the outside through an air outlet valve when the rubber ball is compressed. On the other hand, when the rubber ball is released or permitted to decompress, air is drawn in through the gas analyzing test tube. This known air conveyor, however, has the disadvantage that the quantity of gas conveyed differs from one actuation of the rubber ball to the other, because the volume is a function of the various ways in which the rubber ball is compressed. Furthermore, the suction curve of the rubber ball has a discontinuity, at which a large amount of air is drawn in.

Another type of air conveyor for gas test tubes is disclosed in W. German Pat. No. 1,007,523, in which a bellows is used as the suction element instead of the rubber ball pump in order to reduce the discontinuity in the transport of air. The bellows are arranged between two holding plates, which must be pressed together by the hand of the operator against the action of two compression springs positioned in the bellows in order to empty the bellows and to prepare it for its suction phase. The disadvantage of this conveyor is that the two holding plates are not always pressed together completely or are pressed together only to a certain angle, with the result that the bellows will not be completely emptied. Consequently, in this type of air conveyor as well as the other, the amount of gas conveyed will differ from one actuation to another. There is the further disadvantage that the air conveyor is difficult to operate because it can slip out of the hand of the operator under the effect of the compression springs when it is operated with one hand.

The known air conveyors of the type just described must be actuated several times for one test, because the gas must be drawn several times through the gas tube. For that purpose, the air conveyors have a counter ring which is purely a marking to aid in indicating the number of strokes made with the rubber ball pump. This means that it is easy to make mistakes in the count and thus fail to execute the predetermined number of suction strokes. In the air conveyor of the bellows type, discussed above, it is known to include a stroke counter which is actuated when the two holding plates are compressed. However, because these plates are not positively guided in parallel, especially when they are operated by a single hand, it is possible that the counter is not actuated by the holding plate which makes the count. Furthermore, because of the rocking movements of the bellows, the stroke counter can be actuated even though a correct suction has not been accomplished, that is, the suction stroke actually executed does not correspond to the full suction volume of the bellows. And finally, especially when the device is operated by a single hand, it is possible for the suction stroke to be braked by the hand, because both holding plates must be gripped in the same hand.

It is crucial for the purpose of accurate measurement that the suction volume be the same for each stroke. This is not achieved either with the suction ball or with the known bellows—both are only approximations. In addition, the suction characteristic of each stroke, must be the same, which is not the case with the known air conveyors. For example, in the air conveyor according to W. German Pat. No. 1,007,523, the manual grip on the two holding plates must be completely released in order to release the bellows, so that the holding plates are not braked as they move apart. As soon as there is any braking action on the movement of the holding plates, the suction pressure is no longer constant, and the resulting measurement inaccurate. Finally, it is necessary for the amount of time which elapses during the suction stroke to be the same for each measurement. When the suction stroke is impeded through the incomplete release of the bellows, inaccurate measurements again occur.

Accordingly, it is an object of the invention to provide an air conveyor for gas test tubes of the type discussed above in which the air from the suction element is expelled in a complete, precisely defined, and non-manipulatable manner before a suction stroke can be executed; in which counting errors are eliminated for the sequence of individual suction processes; and in which the suction element can be operated continuously and freely with a constant suction capacity, with identical suction characteristics, and with equal suction times.

SUMMARY OF THE INVENTION

The present invention overcomes the problems inherent in prior art suction devices. In general the present invention is an air conveyor for gas test tubes for the detection of foreign gases or suspended substances in air. The instrument body is designed as a handle for the conveyor and the suction element is a bellows having a bottom plate to which is connected a control rod guided in a channel. The control rod can be stopped when the bellows is empty and released to initiate the suction stroke of the bellows by rotation of a counter ring. Triggered by the rotational movement of a counter ring, a precisely difined volume of air is drawn through the gas analysis test tube so that during this process, air is conveyed continuously under the effect of the bellows.

According to the invention, the bottom plate is coupled by way of the control rod guided in the through-channel of the instrument body with the counter ring so that the bellows can be precisely stopped in its empty position and released again for initiating the suction stroke by rotating the counter ring which is coupled with the actuation of the bellows. Because the bellows is stopped when empty, this position is clearly identified and the suction stroke for a measurement is initiated by the rotation of the counter ring. The bellows is stopped prior to the measurement by means of the control rod. In this way the operator has time to initiate the measurement process by releasing the control rod, that is, by rotating the counter ring. Thus, the number of suction strokes of the bellows is coupled with the number of suction strokes indicated on the counter ring. The continuity of the suction stroke is brought about here by the use of the bellows as the suction element.

Finally, the design of the instrument body as a handle facilitates one-handed operation, because the counter ring, which can be turned around the axis of the instrument body, can be actuated by the thumb and index finger of the hand of the operator which holds the unit.

An especially advantageous is the use of radially biased cam means for arresting the control rod. Also, a window is also provided in the body of the unit, through which a mark on the control rod is visible when the bellows is completely full. Because the control rod is eccentrically positioned in the body of the unit, the stressing means for the control rod and the counter ring with its locking element can be housed in the body at the most convenient cross sectional position, i.e., with a diameter of, for example, 42 mm.

Other advantages of the invention will become apparent from a perusal of the detailed description of a presently preferred embodiment of the invention in connection with the accompanying drawings.

DESCRIPTION OF THE DRAWINGS

FIG. 1 shows a longitudinal section through the air conveyor of the present invention showing the bellows completely full of gas;

FIG. 2 is a longitudinal section through the air conveyor with an empty bellows and with the control rod arrested;

FIG. 3 is a cross section through the body of the air conveyor taken along line III—III and showing the counter ring and the means for arresting the control rod located underneath the counter ring; and FIG. 4 is an elevational view of the air conveyor with a completely full bellows.

PRESENTLY PREFERRED EMBODIMENT

Referring to FIGS. 1 and 2, air conveyor for gas test tubes 1, which serves to detect foreign gases or suspended matter in air, consists of an instrument body 2 preferably made of plastic with a through-channel 3. A suction element 4 is provided, preferably in the form of a bellows. Control rod 5, and a counter ring 6 with stop means 7 for arresting the control rod 5 is associated with ring 6.

Through-channel 3 is eccentrically located in body 2 of the unit, as is more clearly shown in FIG. 3. Through-channel 3 has at one end a sealing element 8 preferably of an elastic, rubber material for gas test tube 1. A sleeve nut 9 of plastic holds sealing element 8 and counter ring 6 firmly on instrument body 2. In addition, bellows 4 made of rubber-elastic material, is rigidly flanged at the other end of the through-channel 3 to end surface 10 of instrument body 2. Bellows 4 is provided with a base plate 11 in which an air outlet valve 12 is provided. Valve 12 allows air or gas to escape when bellows 4 is compressed (FIG. 2), and is closed during the suction stroke of bellows 4. A cylindrical compression spring 13 extends around control rod 5 inside bellows 4. Spring 13 is supported at one end by base plate 11 of the bellows and at the other by end surface 10 of the instrument body 2.

Bellows 4 is circular in cross section and preferably of a diameter that corresponds essentially to the diameter of the instrument body 2. Body 2 is designed as a handle of the conveyor so that the diameter and length are proportioned in that a human hand can easily encompass the instrument body 2 between counter ring 6 and the end surface 10. Counter ring 6 is designed and positioned to be acuated with the thumb and index finger.

Control rod 5, which is permanently connected to the base plate 11 and preferably forms an integral part of it, is movably guided in through-channel 3. These two parts are sized to provide a sliding fit. A longitudinal groove 14 is provided in control rod 5 to prevent it from being turned in the wrong direction during movement. Groove 14 is guided by longitudinal projection 15 which projects from the wall of through-channel 3. A longitudinal groove 16 in channel 3, and entendly along its entire length serves as a gas channel to provide continuous connection between the interior of bellows 4 and the opening in the sealing element 8 for gas test tube 1.

Control rod 5 is provided at its free end 17 with a radial hole 18 for holding a radially directed, spring-loaded stop cam 19. Radial latching recesses 20 and 21 are provided in the wall of the through-channel for the two end-positions, respectively, of the control rod 5, as shown in FIGS. 1 and 2. When bellows 4 is completely full (FIG. 1), stop cam 19 engages in latching recess 21 located near end surface 10 of instrument body 2. Latching recess 21 has an upward-slanting surface 22 pointing in the direction of latching recess 20 to make it easy to release the latched position in order to empty bellows 4.

The spring-loaded locking element 23 of counter ring 6 is guided movably in a radial direction in the other latching recess 23, which is a radial hole located underneath counter ring 6. This locking element consists of a pin 25 provided with a plate 24, and a radially outward-directed compression spring 26 places around pin 25. Plate 24 is supported against rubber seal 27, which surrounds locking element 23 in a cup-like manner thus sealing off throughchannel 3 to the outside. Counter ring 6 is provided on its lower side with ball notches 28. Each ball notch 28 has a number from 1 to 10 correlated with it on the outside of ring 6 as shown in FIG. 4. In one of the ball notches 28 there is a locking ball 29 which is surrounded by a ball guide ring 30 screwed into instrument body 2.

In the area of the radial latching recess 21 for the end position of the control rod for an empty bellows 4, there is gas tight view window 31 positioned through the wall of instrument body 2. Control rod 5 carried at its free end 17 marks 32 on the side opposite the top cam 19 so that these marks are aligned with the visible through window 31 when bellows 4 is completely full (FIGS. 1 and 4).

METHOD OF OPERATION

In the starting position, shown in FIG. 1, bellows 4 is completely full. A gas test tube 1 is inserted into sealing element 8. Instrument body 2 is taken in the hand of the operator, and base plate 11 of bellows 4 is pressed against a solid object or against the upper part of the leg of the operator to compress and empty bellows 4. The air in the bellows escapes through the air outlet valve 12. Stop cam 19 is easily forced out of latching recess 21 by sliding down slanted surface 22. Control rod 5 slides in channel 3 and stop cam 19 is arrested in latching recess 20 when the end-position is reached (FIG. 2). In this way a signal is given to the operator that bellows 4 is completely empty. Rotating counter ring 6 forces the locking ball 29 against the spring-loaded locking element 23 by means of radial crosspieces 33 located between ball notches 28. Locking element 23 in turn presses against stop cam 19 in the control rod 5. This cam is forced out of its latching recess 20 and bellows 4 is actuated by means of the action of the compression spring 12. Air is now drawn in through gas test tube 1, through channel 3 or the parallel longitudinal groove 16, and into the interior of the bellows 4. During this period the air outlet valve 12 is closed. A precisely defined volume of air is thus drawn through the gas test tube 1 by means of a continuous suction stroke which depends only on the characteristic of the compression spring 13. This occurs until mark 32 is aligned with window 31, whereupon stop cam 19 is guided into its latching recess 21. Here the operator is able to recognize that the stroke of bellows 4 has been completed.

The air conveyor for gas test tubes 1 in accordance with the invention has the same suction volume, the same suction characteristic and the same suction time for every suction stroke of bellows 4. For each suction stroke, the same amount of gas is drawn through the gas test tube in the same period of time and with a reproducible velocity characteristic. The control rod 5 latches directly in the gas medium. The air conveyor can be held in the pretensioned, ready-to-measure-state as shown in FIG. 3 at a measurement location not accessible to conventional units, which have to be actuated directly at the measurement site. The variable-length gas channel 3 and 16 has a positive effect on the suction characteristic, in that the decreasing suction resistance of the gas channel 3 and 16 opposes the characteristic of the spring 13 in bellows 4.

While a presently preferred embodiment of the invention has been shown and described in particularity, the invention may be otherwise embodied within the scope of the appended claims.

What is claimed is:

1. An air conveyor for gas test tubes used in the detection of foreign gases or suspended matter in air comprising an instrument body having a channel and at one end a sealing element for connecting the gas test tube to said conveyor and at said other end a suction element; a base plate to which said suction element is mounted and having an air outlet valve therethrough and in communication with said suction element; counter ring means mounted to and rotatable about said body, said ring means including a spring-loaded locking element; a control rod connected to said base plate and positioned for guided movement in said channel, said control rod being arrestable when said suction element is empty and releasable to initiate a suction stroke of said suction element by rotation of such counter ring.

2. An air conveyor according to claim 1, wherein said suction means is a bellows and said instrument body is configured as a handle.

3. An air conveyor according to claim 2, wherein said bellows is circular in cross section and has a diameter corresponding to the instrument body designed as a handle.

4. Air conveyor according to claim 2, wherein said bellows is provided with at least one cylindrical compression spring extending around said control rod, said spring being supported on said base plate and the end surface of said instrument body opposite from said base plate.

5. An air conveyor according to claim 2, wherein said control rod is positively guided in said through-channel and said through-channel includes a longitudinal groove to provide a passageway for gas.

6. An air conveyor according to claim 2, wherein said control rod is provided at its free end with a radial hole adapted to hold a radially directed, spring-loaded stop cam, a spring loaded stop can positioned in said rod and a pair of radial latching recesses positioned in said through-channel to engage said stop cam at the two end-positions of the control rod travel.

7. An air conveyor according to claim 6, wherein a springloaded locking element is provided in said counter ring means, said locking element is supported with radial freedom of movement in the radial latching recess of the said spring-loaded stop cam for the control rod when said bellows is empty, wherein said counter ring includes on its lower side with ball notches and locking balls for mechanically connecting said ring with said locking element.

8. An air conveyor according to claim 7, wherein a rubber seal is provided between said locking ball and said locking element.

9. An air conveyor according to claim 6, wherein gas tight view window is provided in the wall of said instrument body adjacent said radial latching recess for the end-position of control rod when the bellows is full and that control rod is carried at its free end on the side opposite the stop cam marks which, when the bellows is completely full, are aligned with the view window.

10. An air conveyor according to claim 1, wherein said control rod is arranged eccentrically in the instrument body.

* * * * *